United States Patent
Webster, Jr.

[11] Patent Number: 5,626,136
[45] Date of Patent: May 6, 1997

[54] ELECTROPHYSIOLOGY CATHETER WITH PRE-CURVED CIRCULAR TIP

[75] Inventor: Wilton W. Webster, Jr., Altadena, Calif.

[73] Assignee: Cordis Webster, Inc., Baldwin Park, Calif.

[21] Appl. No.: 485,963

[22] Filed: Jun. 7, 1995

Related U.S. Application Data

[63] Continuation-in-part of Ser. No. 55,194, Apr. 28, 1993, abandoned.

[51] Int. Cl.$^6$ ............................................. A61B 5/0402
[52] U.S. Cl. ................................................. 128/642
[58] Field of Search ............................. 128/642, 712; 607/122, 125, 126

[56] References Cited

U.S. PATENT DOCUMENTS

| | | | |
|---|---|---|---|
| 4,777,955 | 10/1988 | Brayton et al. | 128/642 |
| 4,882,777 | 11/1989 | Narula | 607/122 |
| 4,920,980 | 5/1990 | Jackowski | 128/642 |
| 4,960,134 | 10/1990 | Webster, Jr. | 128/642 |
| 5,170,787 | 12/1992 | Lindegren | 128/642 |
| 5,255,679 | 10/1993 | Imran | 128/642 |
| 5,263,493 | 11/1993 | Avitall | 607/122 |
| 5,275,162 | 1/1994 | Edwards et al. | 128/642 |
| 5,354,297 | 10/1994 | Avitall | 607/122 |
| 5,445,148 | 8/1995 | Jaraczewski | 128/642 |

FOREIGN PATENT DOCUMENTS

| 4025369 | 2/1991 | Germany | 128/642 |
|---|---|---|---|

*Primary Examiner*—Lee S. Cohen
*Attorney, Agent, or Firm*—Christie, Parker & Hale, LLP

[57] ABSTRACT

An electrode catheter for mapping right sided supraventricular accessory electrical pathways comprises an elongated tubular catheter body and a tip portion which comprises a compound curve. The compound curve has a first bend and a second bend which forms a generally circular curve. The plane of the generally circular curve lies transverse to and preferably at an angle of about 30° to the axis of the catheter body. The generally circular curve portion of the tip portion carries a plurality of electrodes. A puller wire extends through the catheter body and into the tip portion, the distal end of the puller wire being fixedly attached to the distal end of the tip portion. A handle is provided at the proximal end of the catheter for controlling longitudinal movement of the puller wire relative to the catheter body. Proximal movement of the puller wire relative to the catheter body results in the angle of the first bend becoming more acute and a decrease in the diameter of the generally circular curve of the tip portion.

22 Claims, 4 Drawing Sheets

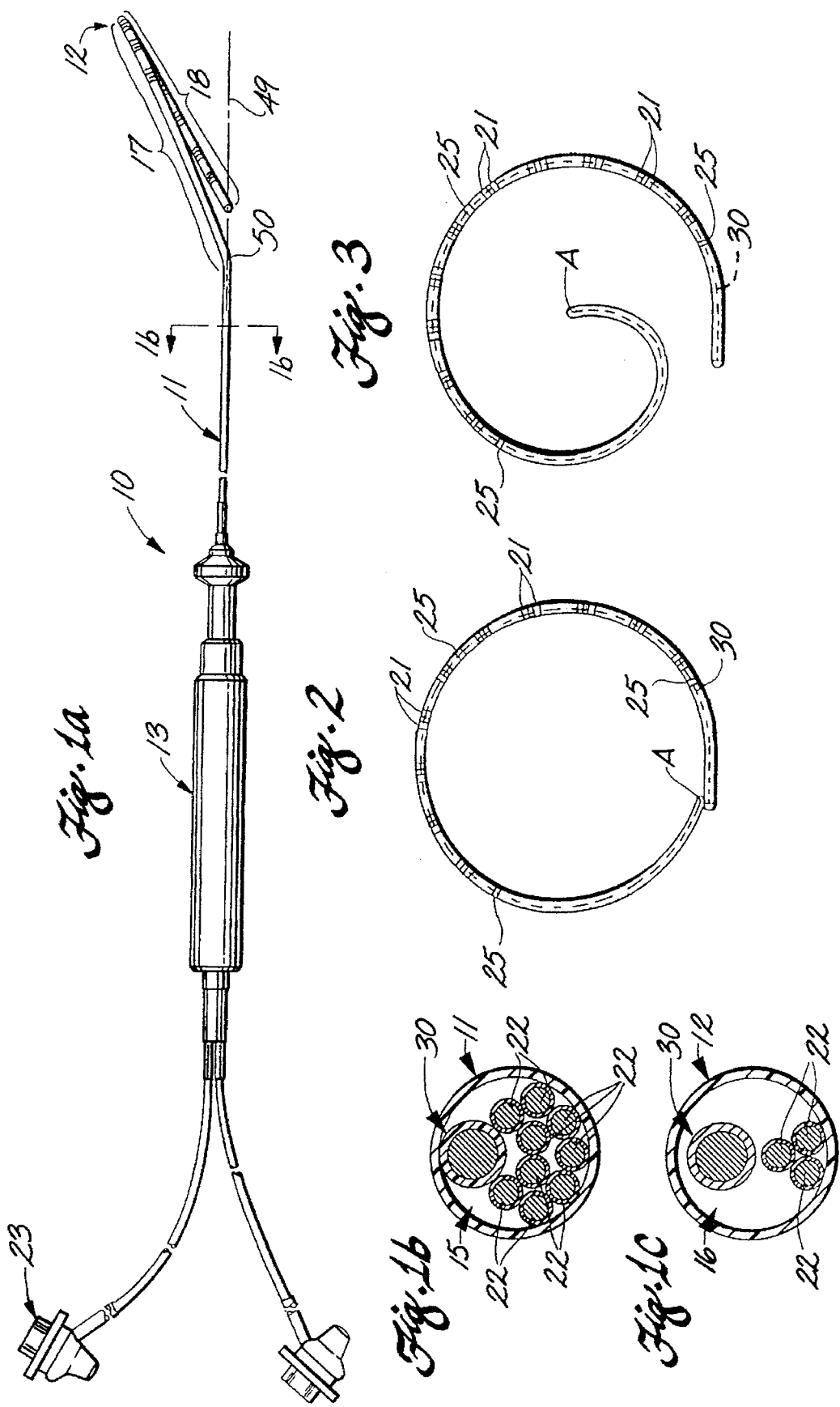

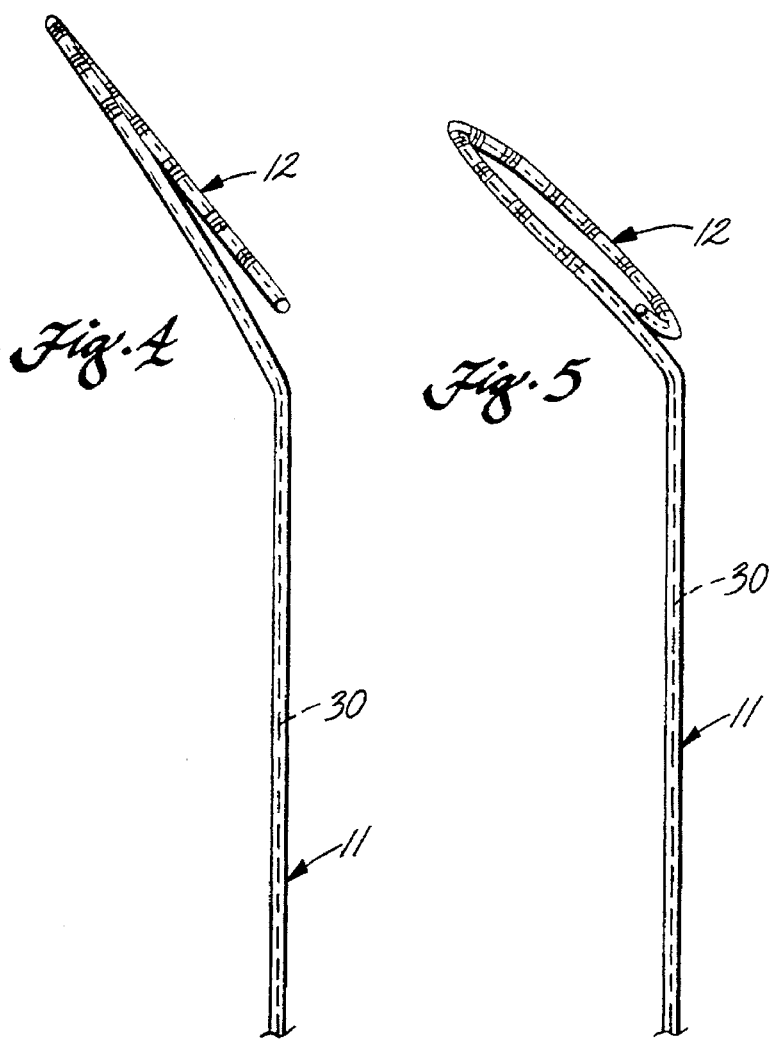
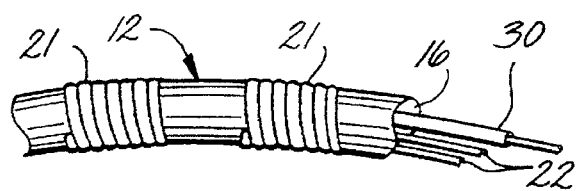

*Fig. 7*
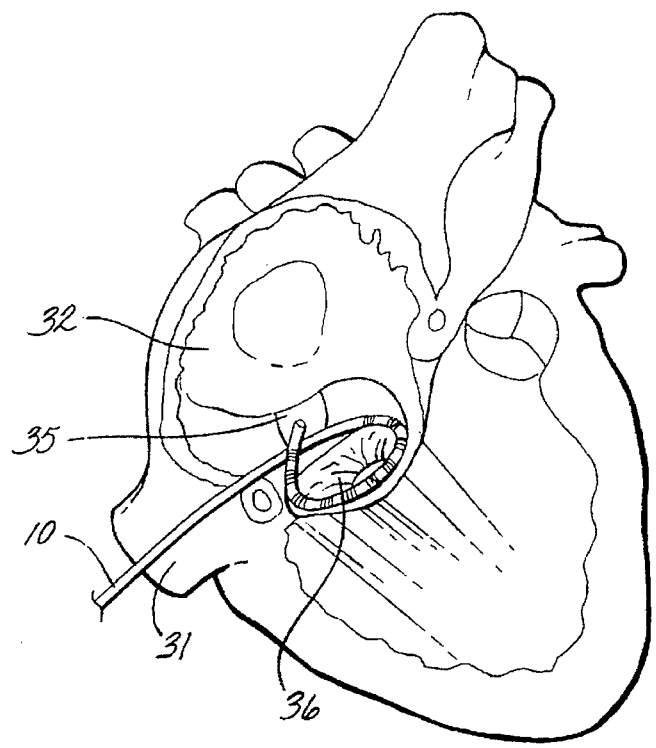
*Fig. 8*
*Fig. 9*
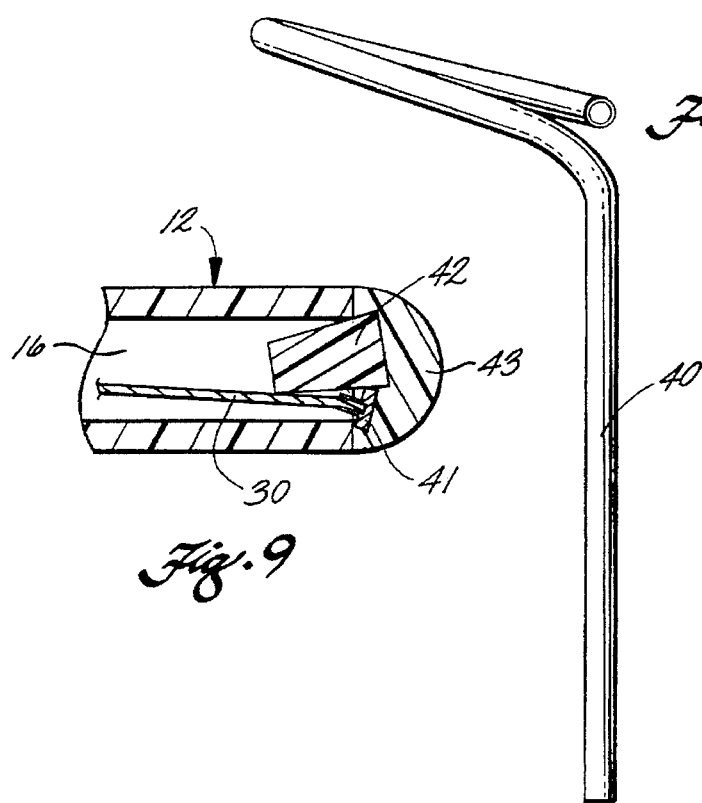

ELECTROPHYSIOLOGY CATHETER WITH PRE-CURVED CIRCULAR TIP

CROSS-REFERENCE TO RELATED APPLICATION

This is a continuation-in-part of application Ser. No. 08/055,194 filed Apr. 28, 1993, now abandoned, the priority filing date of which is hereby claimed and the subject of which is hereby incorporated by reference as if set forth in full.

FIELD OF THE INVENTION

This invention relates to an electrophysiology mapping catheter having a precurved tip and more specifically to an electrophysiology mapping catheter having a generally circular tip portion, the diameter of which can be adjusted by manipulation of a puller wire.

BACKGROUND OF THE INVENTION

Millions of people suffer from abnormally high heart beat rhythm, a condition referred to as "tachycardia." One type of tachycardia is right sided supra-ventricular tachycardia (SVT). This condition is caused by a conducting pathway between the right atrium at the right ventricle across the tricuspid annulus. With right sided supra-ventricular tachycardia, the atria typically beats too rapidly. Symptoms of right sided supra-ventricular tachycardia include chest pain, fatigue and dizziness.

Radiofrequency (RF) catheter ablation has been found to be a safe and efficacious means of interrupting accessory electrical pathways which result in tachycardia. In such a procedure, a special electrophysiology catheter is guided through a vein into the patient's heart and to the site of the accessory pathway. The catheter is designed to transmit energy from an external source into the accessory pathway in an amount sufficient to ablate the tissue. The ablated tissue is replaced with scar tissue which interrupts the accessory pathway. The normal conduction of electroactivity is thereby restored.

Before an RF catheter ablation procedure can be utilized, the site of the accessory pathway must be determined. This is accomplished with a diagnostic or mapping catheter which typically comprises multiple electrodes for stimulating and sensing electrical activity. In, general, this procedure involves introducing a mapping catheter into the patient's heart and into the chamber where the arrhythmia condition exists. The tissue is stimulated in a manner intended to induce the arrhythmia and expose the abnormal electrical conduction. The resulting information regarding the number and locations of aberrant sites identified and the severity of the abnormality enables the electrophysiologists to determine the appropriate course of treatment. Electrophysiologic evaluation generally involves multiple tests to diagnose the arrhythmia and to assess the potential effectiveness of various treatment strategies.

One procedure for determining the site of right sided supra-ventricular tachycardia is to introduce a mapping catheter into the right coronary artery which extends about the right atrium at about the location of the tricuspid annulus. This procedure is very dangerous and accordingly not favored. Another known procedure is to introduce a deflectable tip mapping catheter into the right atrium and, by manipulation of the catheter, to move the catheter about, particularly around the tricuspid annulus until the accessory pathway is located. This is a time-consuming and cumbersome approach.

An improvement in mapping the right sided supra-ventricular pathways has been the use of a multiple electrode catheter having a generally circular precurved tip portion. Such a catheter is advanced from the femoral vein by Seldinger technique into the right atrium. The distal end of the tip portion is maneuvered into the coronary sinus (C.S.) ostium and the remainder of the circular tip portion is maneuvered into the region of the tricuspid annulus. Through the use of multiple electrodes around the circular tip portion, the time required to map the right sided supra-ventricular pathways is greatly reduced.

While the use of a generally circular tip portion has greatly improved the efficiency of the mapping procedure for right sided supra-ventricular pathways, there are still some difficulties associated with this procedure. First, the circular tip portion of the catheter is difficult to maneuver. Secondly, the diameter of the generally circular tip portion is fixed and therefore cannot be adjusted to accommodate atrial chambers of varying sizes. The catheter tip is also difficult to maneuver, particularly being difficult to anchor the distal end of the tip portion in the CS ostium.

SUMMARY OF THE INVENTION

This invention provides an improved electrode mapping catheter particularly suitable for mapping right sided supra-ventricular accessory electrical pathways in the heart. The catheter comprises an elongated, flexible tubular body having proximal and distal ends. The wall of the catheter body is preferably reinforced with one or more layers, reinforcing, e.g., layers of braided stainless steel mesh.

Extending from the distal end of the catheter body is a tubular tip portion. The tip portion comprises a generally circular curve transverse to the axis of the catheter body. In a preferred embodiment, the tip portion comprises a compound curve including a first bend of about 30° to the catheter body axis and then a generally circular curve lying in a plane about 30° to the catheter body axis.

A puller wire extends through the catheter body and into the tip portion. The distal end of the puller wire is fixedly attached to the wall of the tip portion adjacent the distal end of the tip portion. The proximal end of the puller wire is connected to a handle which provides means for moving the puller wire longitudinally relative to the catheter body. Movement of the puller wire proximally relative to the catheter body results in a decrease in the diameter of the generally circular section of the tip portion and increase in the angle of the plane of the circular tip portion to the axis of the catheter body to more than 30°.

The section of the tip portion comprising the generally circular curve carries a plurality of electrodes spaced apart from each other. An electrode lead wire is connected at its distal end to each electrode and extends through the interior of the tip portion and catheter body. At their proximal ends, the electrode lead wires terminate in a suitable connector for connection with a stimulator and/or recorder.

BRIEF DESCRIPTION OF THE DRAWINGS

These and other features and advantages of the present invention will be better understood by reference to the following detailed description when considered in conjunction with the accompanying drawings wherein:

FIG. 1a is an external view of a preferred electrode catheter constructed in accordance with the present invention;

FIG. 1b is a cross section of the catheter body in FIG. 1a at plane 1b;

FIG. 1c is a cross section of the catheter tip in FIG. 1a between the third most distal electrode and the fourth most distal electrode;

FIG. 2 is an enlarged end view of the catheter tip portion;

FIG. 3 is an enlarged end view of another embodiment showing the catheter tip portion of another embodiment of the invention;

FIG. 4 is a side view of the tip portion of the catheter of FIG. 1a;

FIG. 5 is a side view of the tip portion shown in FIG. 4; after the puller wire has been moved longitudinally proximally with respect to the catheter body;

FIG. 6 is a fragmentary enlarged view of a portion of the tip portion showing an electrode pair;

FIG. 7 is a cut-away view of a heart showing the positioning of the tip portion about the annulus of the tricuspid valve;

FIG. 8 is a preferred form used in the formation of the compound curve of the tip portion;

FIG. 9 is an enlarged cross-sectional view of the distal end of the tip portion;

DETAILED DESCRIPTION

Figure 10A:
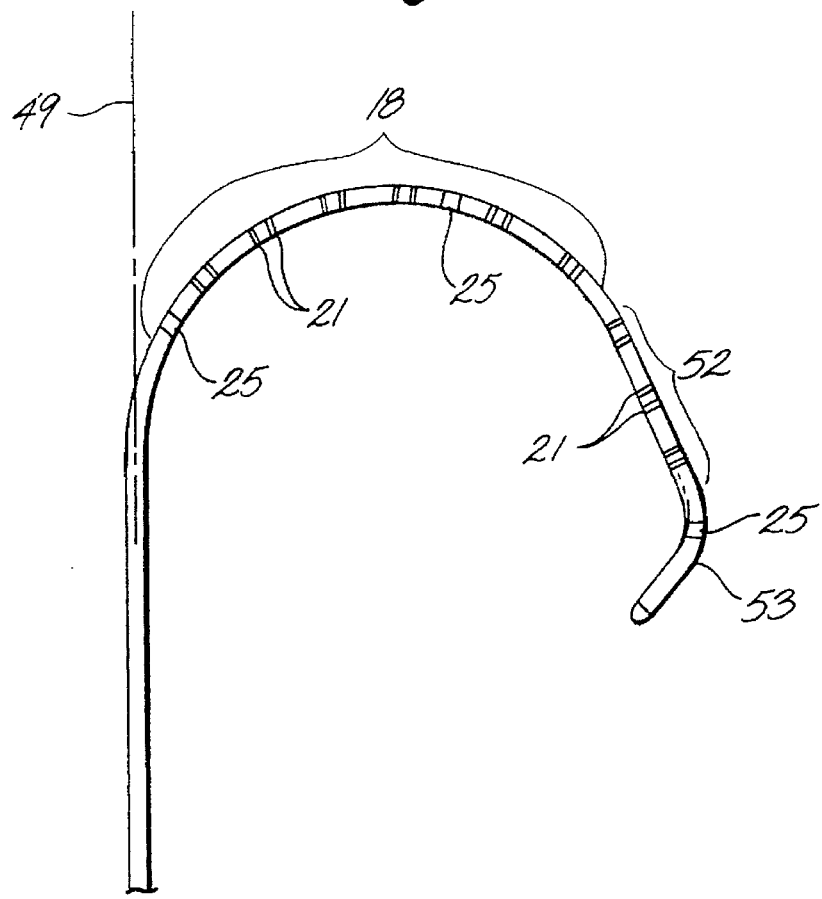
FIG. 10a is an enlarged end view of a further embodiment of the catheter tip portion.

FIGS. 1a, 1b, 1c, and 2 illustrate a preferred electrode catheter constructed in accordance with the present invention. The electrode catheter 10 comprises an elongated catheter body 11 having proximal and distal ends, a catheter tip portion 12 having a generally circular curve transverse, i.e., at an angle 50 to the axis 49 of the catheter body 11 at the distal end of the catheter body 11, and a control handle 13 at the proximal end of the catheter body 11.

The catheter body 11 comprises an elongated tube having a lumen 15. The catheter body 11 is flexible, i.e., bendable, but substantially non-compressible along its length. The catheter body 11 may be of any suitable construction and made of any suitable material. A presently preferred construction comprises a nylon tube surrounded by one or more reinforcing layer of braided stainless steel or the like with a polyurethane coating.

The length and diameter of the catheter body 11 are not critical. For the electrode catheter shown in the accompanying drawing, a length of about 40 to 48 inches, an outer diameter of about 0.1 inch (8 French), and an inner diameter, i.e., lumen diameter, of about 0.03 to about 0.04 inches is presently preferred.

The catheter tip portion 12 comprises a short length, e.g., 8 inches in length and diameter size of 6½ French, of flexible tubing having a lumen 16. The tip portion 12 is formed in a compound curve comprising a first section 17 forming a bend 50 of preferably about 30° from the axis 49 of the catheter body 11, and a second section 18 forming a generally circular curve. Such a compound curve results in the generally circular curve lying generally in a plane transverse to, and preferably about 30° to, the axis 49 of catheter body 11.

As used herein, a "generally circular curve" is meant to include curves which are in and out of a simple plane, spirals, helices, non-circular loops and the like. Such curves may form a full 360° circle or more, but may also be less than a full circle. It is preferred that such curves form at least a semi-circle, i.e., a 180° curve and particularly preferred that the generally circular curve form a full circle, i.e. 360°.

The generally circular curve of the tip portion 12 may be positioned relative to the axis of the catheter body 11 so that the axis A of the catheter body 11 lies on the perimeter of the generally circular curve as shown in FIG. 2 or at any point within the generally circular curve, for example as shown in FIG. 3.

Figure 10B:
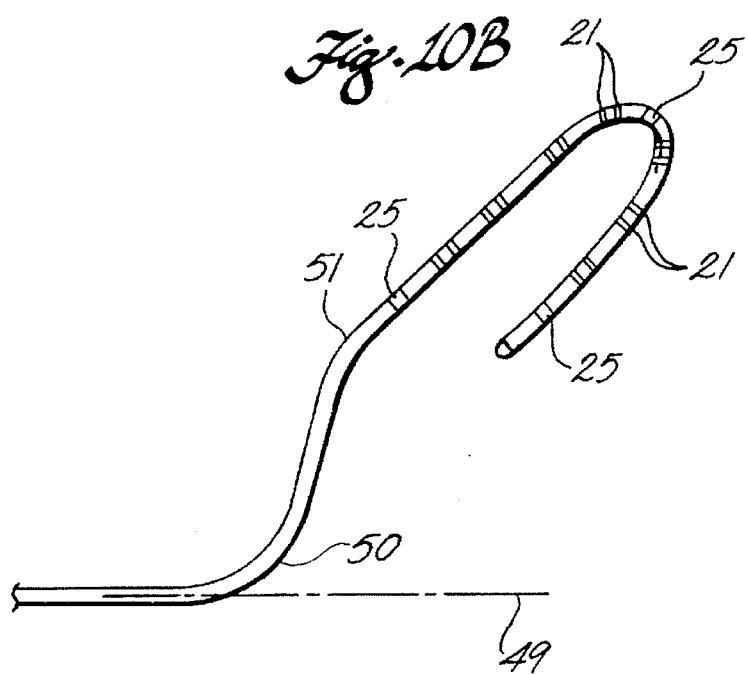
FIG. 10b is a side view of a further embodiment of the catheter tip portion.

In a further embodiment as illustrated in FIGS. 10A and 10B, the second section 18 forming a generally circular curve is substantially semi-circular and the compound curve further comprises a third bend 51 coplanar with the first bend 50 but towards the axis 49 of the catheter body 11 and at a distance that is further from the proximal end of the tip portion 12 than the first bend 50 but substantially equal to the second section 18. Preferably, the first bend 50 is at an angle about 75° from and the third bend 51 is at an angle about 30° towards the axis 49 of the catheter body 11.

When viewed from a vantage point perpendicular to the plane in which the first bend 50 and third bend 51 lie (e.g., FIG. 10B), the first and third bends form an "S" shape to obliquely define the plane in which the second section 18 lies, preferably at an angle about 45° from the axis 49 of the catheter body 11. At the distal end of the generally circular curve, there is a straight section 52 coplanar with the second section 18 forming the generally circular curve but at an angle acute to the axis 49 of the catheter body 11 and having a length not extending beyond the first bend 50. At the distal end of the straight section 52, there is a fourth bend 53 coplanar with the second section 18 toward the proximal end of the tip portion 12.

The tubular wall of the tip portion 12, may be made of any suitable material. It is more compressible and preferably, more flexible, i.e., bendable, than the catheter body 11. A presently preferred construction for the catheter tip portion 12 comprises a thermoplastic resin, e.g., polyurethane, reinforced with a dacron braid. The diameter of the catheter tip portion 12 is not critical, but is preferably about the same as or slightly smaller than the diameter of the catheter body 11.

The compound curve of the catheter tip portion 12 can be formed by any suitable process. In a preferred embodiment, the tubular wall of the tip portion comprises a thermoplastic resin. The catheter is first constructed, e.g., mounting or formation of the electrodes, attachment of the puller wire, etc., without the compound curve in the tip portion, i.e., with the tip portion being straight. The tip portion is then inserted into a tubular, generally rigid form 40 as shown in FIG. 8. The form 40 which may be made of any suitable material, e.g., nylon, has the shape of the desired compound curve. The tip portion of the catheter and the holder are then heated to a temperature sufficient for the tip portion to acquire the shape of the form 40 and to retain that shape when cooled. The form 40 can also be used to contain the tip portion 12 when the catheter is not in use to prevent damage or stress to the tip portion 12.

Along the length of the generally circular section 18 of the tip portion 12, there are a plurality of electrodes 21. The electrodes may be single electrodes or electrode pairs. The electrodes 21 may be in the form of metal rings, preferably platinum rings or platinum iridium alloy rings, the outer diameter of the electrodes 21 being about the same as the outer diameter of the flexible tubing of the tip portion 12 so that the electrodes 21 form a smooth, continuous surface with the outer surface of the flexible tubing. Electrode lead wires 22 having an insulation coating extend from the electrodes 21 through the lumen 16 and 15 of the catheter tip portion 12 and the catheter body 11 and the handle is electrically connected to molded multi-pin connectors 23. The connectors 23 may be plugged directly into a stimulator/recorder or other electrical device or connected to the female end to a floating extension cable which in turn has connectors at its opposite end which can be plugged into the electrical device. It is apparent that the lead wires may be connected to a rotary plug or to individual tip pins if desired.

Alternatively, the electrodes 21 may be formed by passing the electrode lead wires 22 through the wall of the catheter tip portion 12 at separate locations and wrapping the lead wires 22 around the tubing as shown in FIG. 6. The wrapped wires are secured to the wall of the tip portion by adhesive or other suitable means. The insulation coating of the lead wires 22 is stripped off those portions of the wrapped wires which will contact the heart wall. Such a construction is described in U.S. patent application Ser. No. 07/906,546, filed Jun. 30, 1992, which is incorporated herein by reference.

In the embodiment shown, the catheter tip portion 12 carries ten wound electrode pairs 21. Three platinum locator rings or markers 25 are placed equidistant between the fifth and sixth electrode pairs and bordering each end of the electrode array. The marker 25 can be easily distinguished from the electrode pairs under fluoroscopy. This enables identification of the position of each electrode during a mapping procedure. It is understood that the number of electrodes vary as required. The number, location and even presence of a marker or markers is optional.

A puller wire 30, preferably made of stainless steel, extends from the control handle 13 through the lumen 15 of the catheter body 11 and into the lumen 16 of the catheter tip portion 12. In the embodiment shown, the puller wire 30 extends through the lumen 16 of the catheter tip portion 12 and is fixedly attached to the distal tip of the tip portion 12. A preferred anchor means for attaching the puller wire 30 to the catheter tip portion 12 is described in U.S. Pat. No. 4,960,134 which is incorporated herein by reference.

With reference to FIG. 9, there is shown a presently preferred method of attachment. An anchor 41 is fixedly attached, e.g., crimped to the distal end of the puller wire 30. The anchor 41 is then wedged against the tip portion wall and secured at the distal tip of the tip portion by means of plug 42 which is fixed, e.g., glued, in place. The plug 42 and any exposed edges of the anchor 41 are preferably covered with a suitable resin material 43, or the like, to form a rounded distal tip.

Any suitable control handle 13 which can control longitudinal movement of the puller wire 30 relative to the catheter body 11 may be used. A preferred control handle 13, as shown in FIG. 1, is described in U.S. Pat. No. 4,960,134 which is incorporated herein by reference.

Movement of the puller wire 30 rearwardly or proximally relative to the catheter body 11 by manipulation of the control handle 13 results in a tightening of the compound curve of the tip portion 12. Specifically, the bend in the first section 50 of the tip portion 12 becomes more acute and the diameter of the generally circular curve of the second section 18 of the tip portion 12 decreases. FIG. 4 shows the catheter tip portion 12 in its normal state, i.e., before the puller wire 30 is moved proximally relative to the catheter body 11. FIG. 5 shows the effect on the tip portion 12 of moving the pulling wire 30 proximally relative to the catheter body 11.

In use, the catheter 10 is preferably inserted into the femoral vein by conventional technique and is advanced through the inferior vena cava 31 into the right atrium 32. The distal end of the tip portion of the catheter is maneuvered into the coronary sinus ostium 35 and the generally circular section 18 of the tip portion is maneuvered so as to lie about the periphery of the tricuspid valve 36. Heretofore, such maneuvering has been difficult and time consuming. The ability to adjust the diameter of the generally circular section of the tip portion greatly enhances the ability to accomplish the desired maneuvers. It also allows the generally circularly section of the tip portion to be adjusted to better fie the varying sizes of heart patients.

The preceding description has presented with reference to a presently preferred embodiment of the invention shown in the drawings. Workers skilled in the art and technology to which this invention pertains will appreciate that alterations and changes in the described structures can be practiced without meaningfully department from the principal, spirit, and scope of this invention.

Accordingly, the foregoing description should not be read as pertaining only to the precise structures described and shown in the accompanying drawings, but rather should be read consistent with and as support to the following claims which are to have their fullest and fair scope.

What is claimed is:

1. An elongated electrode catheter comprising:

an elongated flexible tubular catheter body having an axis and proximal and distal ends;

a tubular tip portion at the distal end of the tubular body having a preformed generally circular curve transverse to the axis of the catheter body, said tip portion having proximal and distal ends and carrying a plurality of spaced apart electrodes;

an electrode lead wire associated with each electrode, said electrode lead wire having proximal and distal ends and extending through the catheter body and into the catheter tip portion, the distal end of the electrode lead wire being electrically connected to its associated electrode;

a puller wire having proximal and distal ends extending through the tubular body and into the tip portion, the distal end of the puller wire being fixedly attached to the distal end of the tip portion, whereby longitudinal movement of the puller wire relative to the tubular body results in contraction of the generally circular curve; and handle means connected to the proximal ends of the catheter body and puller wire for moving the puller wire longitudinally relative to the catheter body to thereby control the diameter of the generally circular curve of the tip portion.

2. An electrode catheter as claimed in claim 1, wherein the plane of the generally circular curve of the tip portion is at an angle of about 30° to the axis of the tubular catheter body.

3. An electrode catheter as claimed in claim 1, wherein the preformed generally circular curve is substantially semi-circular with a straight section at an angle acute to the axis of the catheter body and an inward bend at the distal end of the tip portion, the curve lying in a plane defined obliquely from the axis of the catheter body.

4. An electrode catheter as claimed in claim 3, wherein the plane of the generally circular curve of the tip portion is at an angle of about 45° from the axis of the tubular catheter body.

5. An electrode catheter as claimed in claim 1, wherein the plurality of spaced apart electrodes comprise platinum ring electrodes.

6. An electrode catheter as claimed in claim 1, wherein the catheter body comprises a nylon tube surrounded by at least one reinforcing layer of braided stainless steel with a polyurethane coating and the tip portion comprises a thermal plastic resin reinforced with a dacron braid.

7. An electrode catheter as claimed in claim 6, wherein the catheter body has an outer diameter of about 8 French and the tip portion has an outer diameter of about 6½ French.

8. An electrode catheter as claimed in claim 1, wherein the handle means is electrically connected to a connector for connecting the electrode catheter to an external electrical device, each electrode lead wire extending through the handle means and into a proximal end of the connector.

9. An electrode catheter as claimed in claim 8, wherein the connector comprises a rotary plug.

10. An electrode catheter as claimed in claim 8, wherein the connector comprises a plurality of individual tip pins, each pin being electrically connected to its associated electrode lead wire.

11. An electrode catheter as claimed in claim 1, wherein the tubular tip portion further comprises a plurality of locator rings bordering each end of and centered therebetween the plurality of spaced apart electrodes.

12. An electrode catheter as claimed in claim 1, wherein the puller wire comprises a stainless steel puller wire.

13. An electrode catheter as claimed in claim 12, wherein the puller wire is fixedly attached to the distal end of the tip portion with a plug glued in place and covered with a resin material forming a rounded distal tip.

14. An elongated electrode catheter comprising:

an elongated flexible tubular catheter body having an axis and proximal and distal ends;

a tubular tip portion at the distal end of the tubular body comprising a compound curve having a first bend away from the axis of the catheter body and a second bend having a preformed generally circular curve transverse to the axis of the catheter body, said tip portion having proximal and distal ends and carrying a plurality of spaced apart electrodes;

an electrode lead wire associated with each electrode, said electrode lead wire having proximal and distal ends and extending through the catheter body and into the catheter tip portion, the distal end of the electrode lead wire being electrically connected to its associated electrode;

a puller wire having proximal and distal ends extending through the tubular body and into the tip portion, the distal end of the puller wire being fixedly attached to the distal end of the tip portion, whereby longitudinal movement of the puller wire relative to the tubular body results in contraction of the preformed generally circular curve; and handle means connected to the proximal ends of the catheter body and puller wire for moving the puller wire longitudinally relative to the catheter body to thereby control the diameter of the preformed generally circular curve.

15. An electrode catheter as claimed in claim 14, wherein the first bend is approximately 30°.

16. An electrode catheter as claimed in claim 14, the preformed generally circular curve being substantially semi-circular and the compound curve further having:

a third bend coplanar with the first bend but towards the axis of the catheter body and at a distance that is further from the proximal end of the tip portion than the first bend but substantially equal to the second bend;

a straight section coplanar with the second bend but at an angle acute to the axis of the catheter body, the straight section having a length not extending beyond the first bend; and a fourth bend coplanar with the second bend towards the proximal end of the tip portion and at the distal end of the tip portion.

17. An electrode catheter as claimed in claim 16, wherein the first bend is approximately 75° and the third bend is approximately 30°.

18. An electrophysiology catheter comprising an elongated flexible tubular catheter body, a plurality of electrode lead wires extending through the catheter body, means for controlling the electrophysiology catheter connected to a proximal end of the catheter body, and an elongated electrode catheter comprising:

a tubular tip portion at a distal end of the catheter body having a preformed generally circular curve transverse to an axis of the catheter body and carrying a plurality of spaced apart electrodes, each such electrode being electrically connected to an electrode lead wire; and a puller wire extending through the catheter body into the tip portion, being fixedly attached to a distal end of the tip portion and being connected at an opposite end to the controlling means, whereby longitudinal movement of the controlling means relative to the catheter body controls the diameter of the generally circular curve of the tip portion.

19. An electrophysiology catheter as claimed in claim 18, wherein the preformed generally circular curve is substantially semi-circular with a straight section at an angle acute to the axis of the catheter body and inward bend at the distal end of the tip portion, the curve lying in a plane defined obliquely from the axis of the catheter body.

20. An electrophysiology catheter as claimed in claim 18, wherein the puller wire comprises a proximal end and a distal end, and wherein an anchor is fixedly attached to the distal end of the puller wire and secured to the tubular tip portion by means for plugging the distal end of the tip portion.

21. An electrophysiology catheter as claimed in claim 18, wherein the controlling means further comprises means for connecting the plurality of electrode lead wires to an external electrical device, the connecting means being electrically connected to a proximal end of each electrode lead wire.

22. An electrophysiology catheter as claimed in claim 18, wherein the tubular tip portion further comprises a plurality of locator rings bordering each end of and centered therebetween the plurality of spaced apart electrodes.

* * * * *